(12) United States Patent
Zevenbergen et al.

(10) Patent No.: US 9,213,013 B2
(45) Date of Patent: Dec. 15, 2015

(54) ELECTROCHEMICAL ETHYLENE SENSOR AND METHOD FOR MONITORING ETHYLENE

(75) Inventors: Marcel Zevenbergen, Rotterdam (NL); Sywert Brongersma, Eindhoven (NL); Mercedes Crego Calama, Geldrop-Mierlo (NL); Daan Wouters, Geldrop (NL)

(73) Assignee: Stichting IMEC Nederland, Eindhoven (NL)

(*) Notice: Subject to any disclaimer, the term of this patent is extended or adjusted under 35 U.S.C. 154(b) by 141 days.

(21) Appl. No.: 13/433,057

(22) Filed: Mar. 28, 2012

(65) Prior Publication Data

US 2012/0247978 A1 Oct. 4, 2012

Related U.S. Application Data

(60) Provisional application No. 61/468,468, filed on Mar. 28, 2011.

(51) Int. Cl.

| | | |
|---|---|---|
| *G01N 27/413* | (2006.01) | |
| *G01N 27/26* | (2006.01) | |
| *G01N 27/404* | (2006.01) | |
| *G01N 33/00* | (2006.01) | |
| *G01N 27/417* | (2006.01) | |

(Continued)

(52) U.S. Cl.
CPC ........ *G01N 27/4045* (2013.01); *G01N 33/0047* (2013.01); *G01N 27/413* (2013.01); *G01N 27/417* (2013.01); *G01N 27/48* (2013.01); *G01N 33/025* (2013.01)

(58) Field of Classification Search
CPC .... G01N 27/413; G01N 27/417; G01N 27/48
USPC .................................. 205/787; 204/431, 414
See application file for complete search history.

(56) References Cited

U.S. PATENT DOCUMENTS 6,828,062 B2 * 12/2004 Lu et al. ....................... 429/213
7,758,735 B2    7/2010 Hengstenberg et al.

(Continued)

FOREIGN PATENT DOCUMENTS

| | | |
|---|---|---|
| GB | 2395564 | 12/2004 |
| GB | 2426343 | 9/2007 |

(Continued)

OTHER PUBLICATIONS

Ong et al. Chem. Mater. 2011, 23, 2979-2986.*
"Electrochemical Methods: Fundamentals and Applications", Bard and Faulker Eds., 1980, John Wiley & Sons.*
Cui et al. (ChemSusChem 2010, 3, 1043-1047).*

(Continued)

*Primary Examiner* — Luan Van
*Assistant Examiner* — Steven Rosenwald
(74) *Attorney, Agent, or Firm* — Knobbe, Martens, Olson & Bear LLP

(57) ABSTRACT

An electrochemical ethylene sensor and method for ethylene sensing are disclosed. In one aspect, an electrochemical ethylene sensor includes a working electrode and a counter electrode on an electrically insulating substrate. An ionic liquid layer covers the working electrode and counter electrode. In one method, a voltage is applied to the working electrode which is equal to or lower than the voltage required for the onset of oxidation of the material of the working electrode, for example, in the range spanning 700 mV before the onset of oxidation of the material of the working electrode.

19 Claims, 18 Drawing Sheets

(51) Int. Cl.
*G01N 27/48* (2006.01)
*G01N 33/02* (2006.01)

(56) References Cited

U.S. PATENT DOCUMENTS

| 2004/0033414 | A1 | 2/2004 | Rohrl | |
|---|---|---|---|---|
| 2005/0045493 | A1* | 3/2005 | Mahurin et al. | 205/775 |
| 2008/0209876 | A1* | 9/2008 | Miller | 55/522 |

FOREIGN PATENT DOCUMENTS

| JP | 2001 289809 | 10/2001 |
|---|---|---|
| JP | 2006 098269 | 4/2006 |
| WO | WO 2004/017443 | 2/2004 |
| WO | WO 2008/098137 A2 | 8/2008 |
| WO | WO 2008/110830 | 9/2008 |
| WO | WO 2010/063626 A1 | 6/2010 |

OTHER PUBLICATIONS

Huang et al., "Toward Membrane-Free Amperometric Gas Sensors: A Microelectrode Array Approach", Analytical Chemistry, 82, 2010, pp. 5238-5245.
The extended European search report for European Patent Application No. 12161869.8 dated Jul. 25, 2012 by European Patent Office.
Database WPI Week 200241 Thomson Scientific, London, GB; AN 2002-374694 XP002679431, Retrieved on Jul. 18, 2012.
Database WPI Week 200630 Thomson Scientific, London, GB; AN 2006-287433 XP002679432, Retrieved on Jul. 18, 2012.
Buzzeo et al., "Use of room temperature ionic liquids in gas sensor design", Analytical Chemistry, American Chemical Society, US, vol. 76, No. 15, Aug. 1, 2004, pp. 4583-4588.
Jordan et al., "Amperometric sensor for monitoring ethylene", Analytical Chemistry, American Chemical Society, US, vol. 69, No. 4, Feb. 15, 1997. pp. 558-562.

* cited by examiner

1(a)

1(b)

4(a)

4(b)

4(c)

4(d)

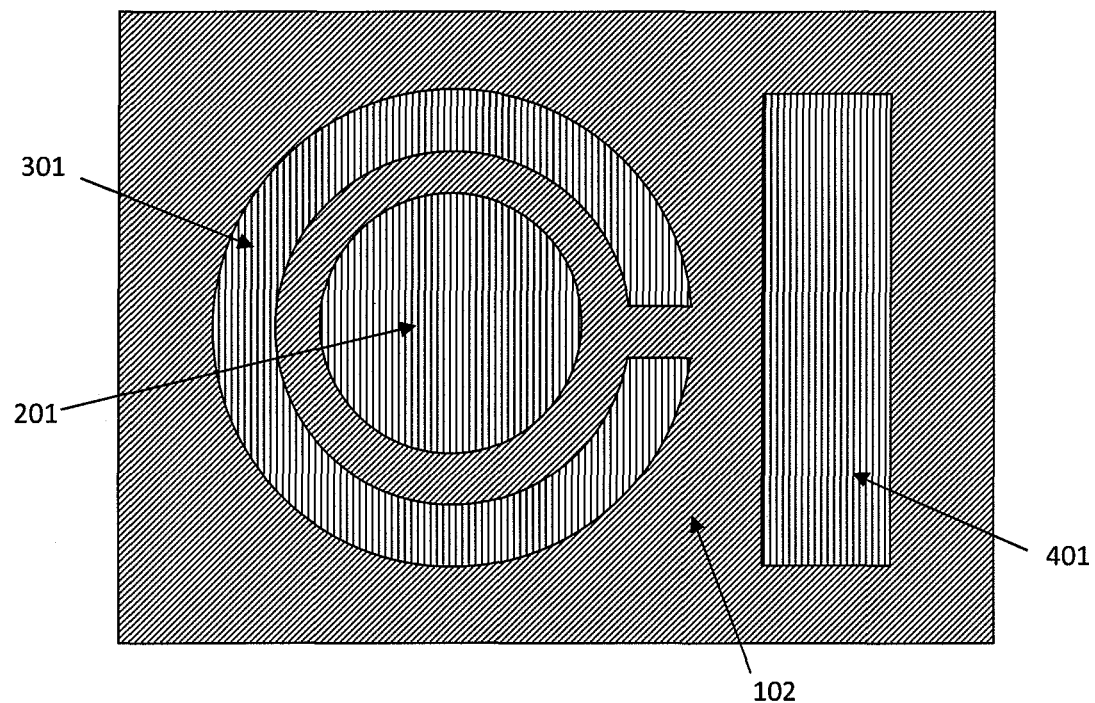
5(a)
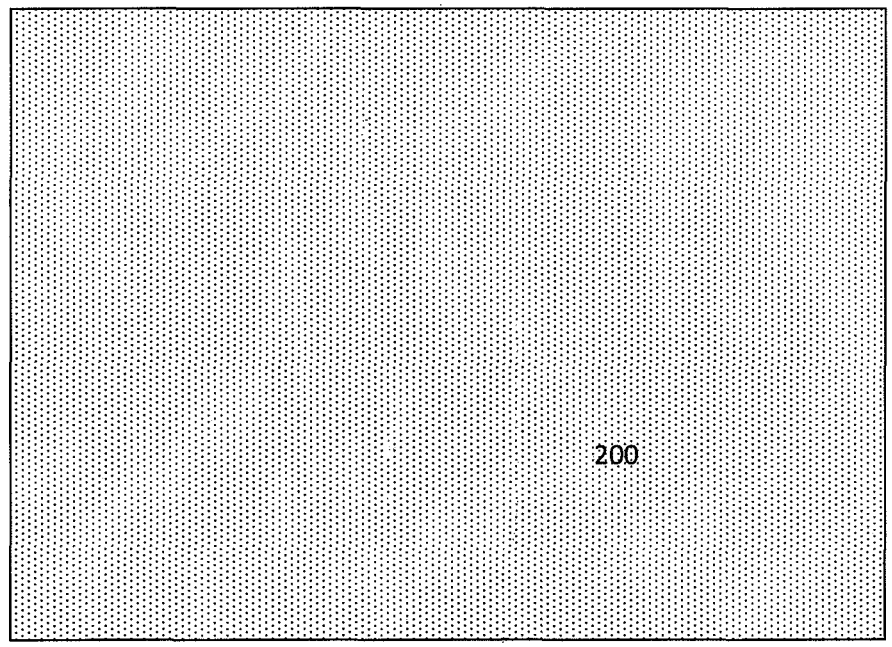
5(b)

5(c)

5(d)

ELECTROCHEMICAL ETHYLENE SENSOR AND METHOD FOR MONITORING ETHYLENE

CROSS REFERENCE TO RELATED APPLICATIONS

This application claims priority under 35 U.S.C. §119(e) to U.S. provisional patent application 61/468,468 filed on Mar. 28, 2011, which application is hereby incorporated by reference in its entirety.

BACKGROUND OF THE INVENTION

1. Field of the Invention

The disclosed technology relates to electrochemical ethylene sensors, to the use of electrochemical sensors for ethylene monitoring, and to methods for ethylene monitoring.

2. Description of the Related Technology

Ethylene monitoring can be very useful in fruit quality control. Ethylene is a plant hormone that is excreted by ripe fruit. It can induce undesired ripening (leading to a reduced lifetime) in other fruits stored in the vicinity. Conversely, ethylene gas is sometimes added into warehouses to artificially induce ripening. Ethylene monitoring is therefore very useful for monitoring fruit freshness.

Ethylene can be oxidized and is therefore amenable for electrochemical detection.

Electrochemical gas detection is based on oxidation or reduction of a target gas at an appropriately biased electrode. An electrochemical gas sensor typically comprises three electrodes: a working electrode, a reference electrode and a counter electrode, the electrodes being in contact with an electrolyte. Before electrochemically reacting at the working electrode surface, the target gas dissolves in the electrolyte. The electrochemical reaction results in an electric current, that is a measure for the amount of gas oxidized or reduced at the working electrode. The power consumption of this type of sensors is intrinsically small and therefore well suited for emerging wireless, ultra-low power autonomous transducer systems.

However, this type of sensors has several disadvantages. For example, for many gases, such as carbon monoxide, hydrogen sulphide, nitric oxide and ethylene, electrochemical detection requires a reservoir filled with a high-molarity acidic electrolyte such as a sulfuric acid solution. This solution is irritating at the concentrations used, thus imposing strict requirements on the reservoir package. Furthermore, the solubility of these gases in water is limited and therefore a large working electrode is required to achieve the desired detection range. The large working electrode in combination with a dangerous concentration of sulfuric acid in the reservoir leads to bulky sensors. In addition, a liquid used as an electrolyte evaporates, which leads to drift and eventually sensor failure.

The first step of the mechanism of electrochemical ethylene sensing consists of ethylene adsorption at the working electrode surface followed by several electron-transfer events. The oxidation of the working electrode at high applied potentials plays a crucial role in the functioning of electrochemical ethylene sensors because it hinders ethylene oxidation. For example, gold is able to oxidize ethylene at room temperature only in an acidic electrolyte, because only in an acid environment a potential window exists in which ethylene oxidation can occur before the onset of gold oxidation.

In food quality monitoring however, the use of a strong acidic electrolyte is undesirable or it would impose strict requirements on the sensor package. There is a need for simple, accurate, cheap and stable ethylene sensors that are small and have low power consumption.

Ethylene can for example be detected and monitored by means of sensors comprising a semiconducting metal oxide layer, wherein the detection is based on measuring the metal oxide resistivity. However, this type of sensors requires an elevated operating temperature, resulting in relatively high power consumption. The response time and the recovery time are relatively large, e.g. in the order of a few minutes.

SUMMARY OF CERTAIN INVENTIVE ASPECTS

Certain inventive aspects relate to an ethylene sensor that allows continuous real-time monitoring of ethylene at ambient temperature, wherein the sensor is small, accurate and stable and has low power consumption.

In one aspect, an ethylene sensor may advantageously be used for real-time monitoring of ethylene concentration in food quality control, e.g. for monitoring fruit ripening.

Certain inventive aspects relate to a method for ethylene monitoring at ambient temperature using a sensor that is small, accurate and stable and has low power consumption.

In a first aspect, there is an electrochemical ethylene sensor comprising: a working electrode and a counter electrode on an electrically insulating substrate; characterized by an ionic liquid layer covering the working electrode and the counter electrode.

The sensor may comprise electrical circuitry for applying a voltage to the working electrode. The applied voltage may be equal to or below the voltage that leads to onset of oxidation of the working electrode material. For instance the electrical circuitry may be adapted to apply a voltage in the range between about 700 mV before the onset of oxidation of the working electrode material and the onset of oxidation of the working electrode material. This range is a range where ethylene will be oxidized at the working electrode and thus can be detected but significant oxidation of the working electrode material does not occur.

In general electrical circuitry applies the voltage to the working electrode by applying a voltage difference between the working electrode and another electrode of the sensor. In some embodiments there may be a separate reference electrode and thus the electrical circuitry may be configured to apply a voltage difference between the working electrode and reference electrode. However the sensor may be a two electrode sensor and thus the voltage may be applied to the working electrode by applying a voltage difference between the working electrode and the counter electrode. In general then a voltage difference may be applied between the working electrode and a reference electrode, which may or may not be the same electrode as the counter electrode.

The electrical circuitry may additionally be configured for measuring a current between the working electrode and the counter electrode.

In some embodiments the working electrode material may be gold.

In one aspect, an ethylene sensor can have a size smaller than about 1 $cm^2$, e.g. a size in the range between about 10 $mm^2$ and 25 $mm^2$. The ionic liquid layer may be a thin layer and the thickness of the thin ionic liquid layer may be in the range between about 1 nm and about 100 micrometer, for example between about 1 micrometer and 100 micrometer. The power consumption can be low, e.g. less than about 1 microWatt, e.g. less than about 10 nanoWatt, even less than about 1 nanoWatt. Ethylene monitoring can for example be performed with an accuracy in the range between about a few ppb and 1000 ppm. The ethylene detection limit can be lower than about 1000 ppb, e.g. lower than about 100 ppb, e.g. about 10 ppb. The sensitivity can be improved by using a thinner ionic liquid layer, by using an ionic liquid gel and/or by adding silver salt to the ionic liquid.

In a second aspect, there is the use of an ionic liquid layer in an electrochemical sensor for ethylene monitoring. Thus one inventive aspect extends to use of an electrochemical sensor comprising at least one electrochemical cell or electrochemical sensing element for ethylene monitoring, wherein the at least one sensing element comprises: a working electrode, a counter electrode and preferably a reference electrode being provided on an electrically insulating substrate, and a thin ionic liquid layer covering the working electrode, the counter electrode and the reference electrode.

In a third aspect, there is a method for monitoring ethylene, the method comprising: applying a voltage to a working electrode and measuring a current between the working electrode and a counter electrode characterized by maintaining a layer of ionic liquid layer covering the working electrode and counter electrode. Applying a voltage to the working electrode may comprise applying a voltage in the range between about 700 mV before the onset of oxidation of the working electrode material and the onset of oxidation of the working electrode material. The method thus may involve providing an electrochemical sensor comprising at least one electrochemical cell or electrochemical sensing element, wherein the at least one sensing element comprises a working electrode, a counter electrode and preferably a reference electrode being provided on an electrically insulating substrate, and a thin ionic liquid layer covering the working electrode, the counter electrode and the reference electrode; applying a fixed voltage difference between the working electrode and the reference electrode; and measuring a current between the working electrode and the counter electrode as a function of time. The fixed voltage difference is selected in the range between about 700 mV before the onset of oxidation of the working electrode material and the onset of oxidation of the working electrode material, preferably in the range between about 400 mV before the onset of oxidation of the working electrode material and the onset of oxidation of the working electrode material, such as for example at about 200 mV before the onset of oxidation of the working electrode material.

Certain objects and advantages of various inventive aspects have been described herein above. Of course, it is to be understood that not necessarily all such objects or advantages may be achieved in accordance with any particular embodiment of the disclosure. Thus, for example those skilled in the art will recognize that the disclosure may be embodied or carried out in a manner that achieves or optimizes one advantage or group of advantages as taught herein without necessarily achieving other objects or advantages as may be taught or suggested herein. Further, it is understood that this summary is merely an example and is not intended to limit the scope of the disclosure. The disclosure, both as to organization and method of operation, together with features and advantages thereof, may best be understood by reference to the following detailed description when read in conjunction with the accompanying drawings.

BRIEF DESCRIPTION OF THE DRAWINGS

FIG. 1(a) shows a cross section; FIG. 1(b) shows a top view of the device.

Figure 1:
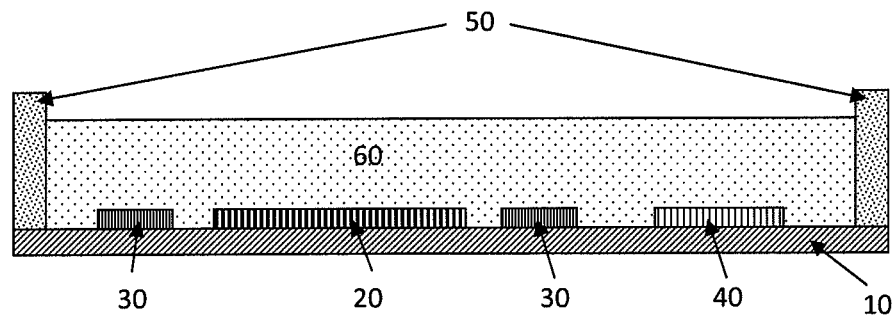
FIG. 1 is a schematic illustration of an electrochemical sensing element comprising a thin layer of an ionic liquid according to one embodiment.
Figure 1:
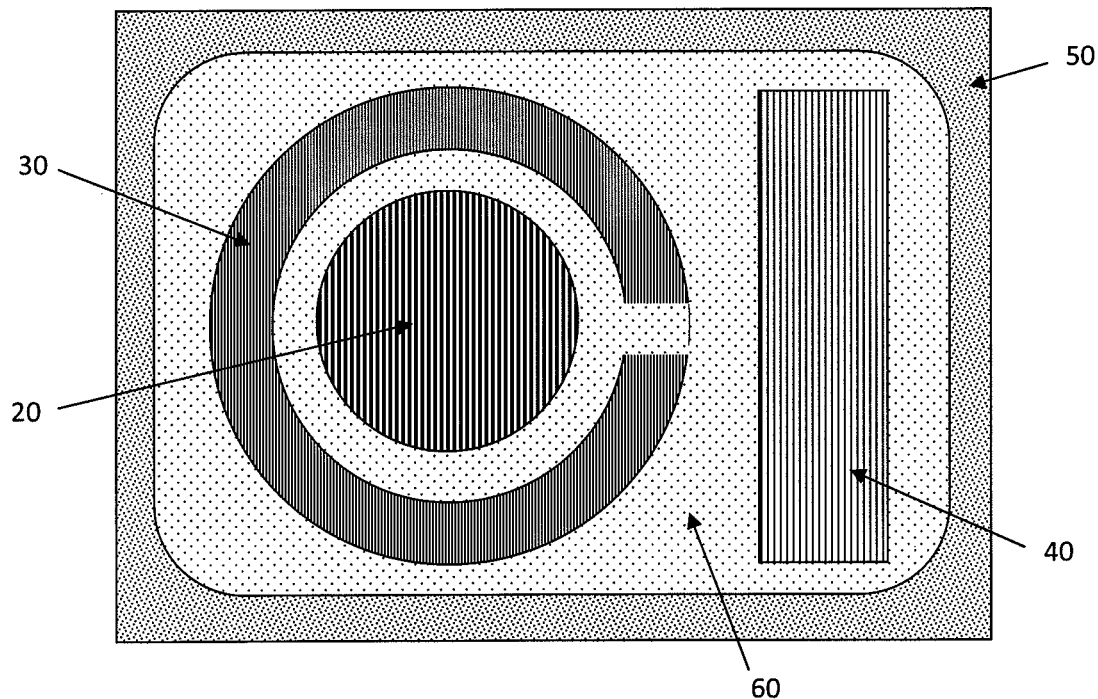

Any reference signs shall not be construed as limiting the scope of the present disclosure.

In the different drawings, the same reference signs refer to the same or analogous elements.

DETAILED DESCRIPTION OF CERTAIN ILLUSTRATIVE EMBODIMENTS

In the following detailed description, numerous specific details are set forth in order to provide a thorough understanding of the disclosure and how it may be practiced in particular embodiments. However, it will be understood that the present disclosure may be practiced without these specific details. In other instances, well-known methods, procedures and techniques have not been described in detail, so as not to obscure the present disclosure. While the present disclosure will be described with respect to particular embodiments and with reference to certain drawings, the disclosure is not limited hereto. The drawings included and described herein are schematic and are not limiting the scope of the disclosure. It is also noted that in the drawings, the size of some elements may be exaggerated and, therefore, not drawn to scale for illustrative purposes.

Furthermore, the terms first, second, third and the like in the description, are used for distinguishing between similar elements and not necessarily for describing a sequence, either temporally, spatially, in ranking or in any other manner. It is to be understood that the terms so used are interchangeable under appropriate circumstances and that the embodiments of the disclosure described herein are capable of operation in other sequences than described or illustrated herein.

Moreover, the terms top, bottom, over, under and the like in the description are used for descriptive purposes and not necessarily for describing relative positions. It is to be understood that the terms so used are interchangeable under appropriate circumstances and that the embodiments of the disclosure described herein are capable of operation in other orientations than described or illustrated herein.

It is to be noticed that the term "comprising" should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B.

Certain embodiments relate to microfabricated electrochemical ethylene sensors wherein a thin layer of ionic liquid is used as an electrolyte, to the use of such sensors for monitoring ethylene, and to methods for monitoring ethylene using such sensors. As opposed to electrochemical sensors based on sulfuric acid in a liquid electrolyte, ionic liquids are non-hazardous and the sensor can be housing-free or a simple housing such as an epoxy layer (as further described) is sufficient for a fully functional electrochemical gas sensor.

An electrochemical ethylene sensor according to one embodiment comprises at least one electrochemical cell or electrochemical sensing element, wherein the at least one sensing element comprises a working electrode, a counter electrode and preferably a reference electrode being provided on an electrically insulating substrate, a thin ionic liquid layer covering working electrode, the counter electrode and the reference electrode, and electrical circuitry for applying a voltage difference between the reference electrode (either a separate reference electrode or the counter electrode) and the working electrode and for measuring a current between a working electrode and the counter electrode. The electrical circuitry is adapted for applying a voltage difference in the range between 700 mV before the onset of oxidation of the working electrode material (e.g. gold) and the onset of oxidation of the working electrode material. The at least one sensing element may comprise a separate reference electrode to overcome a voltage drop (ohmic drop) over the counter electrode. Preferably the reference electrode is provided in close proximity to the working electrode.

One embodiment relates to the use of an electrochemical sensor comprising at least one electrochemical cell or electrochemical sensing element for ethylene monitoring, wherein the at least one sensing element comprises: a working electrode, a counter electrode and preferably a reference electrode being provided on an electrically insulating substrate and a thin ionic liquid layer covering the working electrode, the counter electrode and the reference electrode.

In one embodiment, the miscibility of the ionic liquid with water is preferably limited. Preferably an ionic liquid is selected that can absorb a small amount of water, e.g. up to about 5 w % of water, without affecting the ionic liquid layer's stability. Furthermore, the ionic liquid is preferably stable when exposed to air, has a low viscosity, e.g. in the range between about 1 mPa s and 500 mPa s, and a good solubility of ethylene (at least about 0.1 mol %). An example of an ionic liquid that fulfills these requirements is 1-butyl-3-methylimidazolium bis(trifluoromethylsulfonyl)imide ([BMIM][NTf$_2$]). Another suitable ionic liquid is 1-hexyl-3-methylimidazolium tris(pentafluoroethyl)trifluorophosphate ([HMIM][FAP]). These are just examples of suitable ionic liquids, but the present disclosure is not limited thereto.

In one embodiment, the ionic liquid can be an ionic liquid gel. In such a gel the ionic liquid is contained in a cross-linked matrix such that flowing of the material is inhibited. For example, ionic liquid gels can be made by a combination of polymers and gels. The polymer and the ionic liquid are mutually soluble, and because of the presence of cross-links in the polymer a non-flowing material is formed. In principle any type of cross-link may be used, such as chemical cross-links and physical cross-links. Physical cross-links can be obtained by using a block copolymer instead of a homopolymer. One part of this block copolymer is soluble in the ionic liquid, and the other part of the block copolymer is not soluble in the ionic liquid. These non-soluble parts of many chains cluster together, thus forming physical cross-links. In between the cross-links are the soluble parts of the polymer chains and the ionic liquid. The ionic liquid inside the gel is contained in a fine network and flow is thus prevented. The polymer chains inside the gel are preferably selected such that they do not interfere with the sorption of gaseous analytes and such that they are electrochemically inactive.

An ionic liquid gel has many of the properties of a liquid ionic liquid. It absorbs the target gasses and it is conductive. Because the ionic liquid is contained in a gel form, the concept of viscosity and mass transport inside the gel is completely different than in a liquid. On one hand, the low mobility inside the gel may reduce mass transport and conductivity of the ionic liquid, leading to lower sensor currents compared to sensors having a liquid ionic liquid layer of similar thickness. On the other hand, by using a ionic liquid gel the active layer is present in a more stable form. In addition, the ionic liquid gel can be applied in much thinner films. The gel can for example be applied from a dilute solution (e.g. by drop casting or spin casting) or a thin layer can be deposited for example by inkjet printing. The presence of a thinner layer leads to shorter diffusion distances and thus may (at least partly) compensate for the lower mobility.

As an example of an ionic liquid gel that can be used in a sensor according to one embodiment, an ionic liquid (e.g. [BMIM][NTf2]) and a polymer (e.g. poly(vinylidene fluoride-co-hexafluoropropylene, average Mw ~400,000 (bimodal distribution), average Mn ~130,000, pellets (Aldrich)) are dissolved in acetone. The ratio of polymer to ionic liquid can be up to about 3:7 (i.e. about 70 wt % ionic liquid in the gel). The concentration of polymer in acetone is for example approximately 5 mg/mL or less. However, this is an example and the present disclosure is not limited thereto. Other block copolymers and/or other ionic liquids can be used.

In one embodiment, metal ions such as silver ions or copper ions can be added to the ionic liquid, e.g. to enhance ethylene solubility.

Ionic liquids are basically molten salts at room temperature that completely consist of ions at room temperature and provide electrical connection to the various electrodes in the electrochemical sensor or electrochemical cell. Ionic liquids have several advantages when used as an electrolyte in electrochemical gas sensors. First, some ionic liquids are non-toxic, non-irritating and even biocompatible. Second, the vapor pressure of ionic liquids is very small, such that evaporation of even thin layers of ionic liquid is negligible, leading to stable sensors. Third, the solubility of some gases, such as carbon dioxide, nitrous oxide and ethylene, is higher in ionic liquids than in water. This means that at a given concentration of the analyte, e.g. ethylene, in the gas phase, and in case of equilibrium with ethylene in the gas phase, an ionic liquid contains a higher ethylene concentration than water. A larger sensor response can be expected, because the response usually scales with concentration. The larger concentration of the analyte in the ionic liquid layer alleviates the size requirements for the working electrode, leading to smaller sensors. Finally, ionic liquid layers can be made thin, for example by simply casting a droplet and allow it to spread over a surface, or by encapsulation in a porous layer or by printing. A thinner layer ensures a more efficient mass transport from the gas phase to the working electrode surface and thus leads to a faster response (shorter response time) of the sensor. The response time of the sensor to a gas concentration change depends on the ionic liquid layer thickness as well. The thin layer of ionic liquid allows the sensor to be significantly miniaturized.

Figure 3:
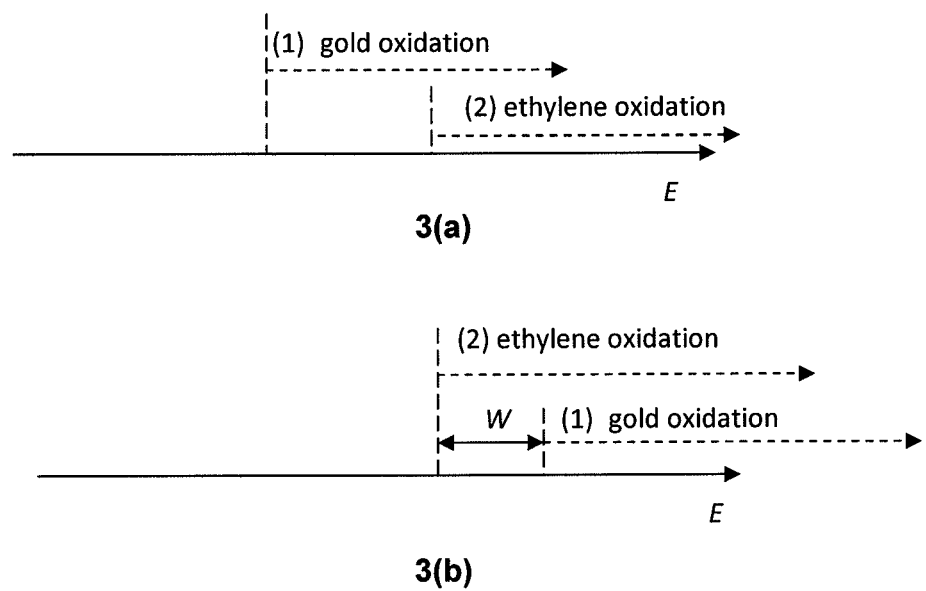
FIG. 3 shows working electrode potentials at which gold oxidation and ethylene oxidation start in a neutral environment (FIG. 3(a)) and in an acid environment (FIG. 3(b)).

It is known that ethylene can be oxidized at a gold electrode in an acid environment, such as for example in water with a large amount of sulfuric acid. When a sufficiently high potential (onset of gold oxidation) is applied to the gold electrode, a layer of gold oxide is formed on the electrode. In a neutral environment, gold oxide formation occurs at a lower potential than ethylene oxidation. The presence of a layer of gold oxide hinders the oxidation of ethylene, i.e. in a neutral environment ethylene cannot react with the gold electrode and thus cannot be detected. In an acid environment, e.g. in the presence of sulfuric acid, the onset of gold oxide formation shifts to a higher potential, thus opening a potential window in which ethylene oxidation can occur. This is schematically illustrated in FIG. 3. FIG. 3 shows working electrode potentials E at which gold oxidation (1) and ethylene oxidation (2) start in a neutral environment (FIG. 3($a$)) and in an acid environment (FIG. 3($b$)). In a neutral environment, gold oxidation occurs before ethylene oxidation and sensing of ethylene is not possible. In an acid environment, the onset of gold oxidation shifts to a higher potential, thereby opening a potential window W in which ethylene can be oxidized and thus detected.

The pH of most ionic liquids is in the range between 5 and 7, which is neutral, and therefore ethylene oxidation is not expected to occur when using an ionic liquid as an electrolyte in an electrochemical sensor with a gold working electrode, because gold oxidation would hinder ethylene oxidation. Therefore, ethylene detection or ethylene monitoring with an electrochemical sensor using an ionic liquid electrolyte is expected to be impossible. However, it was surprisingly found by the inventors that ethylene oxidation is possible with an electrochemical sensor that uses a thin layer of ionic liquid on top of a gold working electrode as illustrated in FIG. 1.

Although certain embodiments are further described for devices comprising a gold working electrode, the present disclosure is not limited thereto. Other suitable working electrode materials may be used, such as for example iridium, palladium, rhodium, osmium, ruthenium platinum or glassy carbon.

FIG. 1 schematically illustrates an electrochemical sensor according to one embodiment. FIG. 1($a$) shows a cross section; FIG. 1($b$) shows a top view. The sensor comprises an electrically insulating substrate 10. The substrate 10 can for example be a silicon substrate covered with a silicon oxide layer or any other material which is electrically insulating and compatible with the semiconductor fabrication and packaging process. The sensor further comprises a working electrode 20. In operation, an analyte (e.g. ethylene) is oxidized at a surface of the working electrode 20. The working electrode material can be a material commonly used in electrochemical sensors, such as for example gold, platinum or glassy carbon. For the detection of ethylene however, gold is preferred above platinum. The electrochemical sensor further comprises a reference electrode 30 and a counter electrode 40 which can be of the same or different material as the working electrode. The reference electrode 30 is provided as close as possible to the working electrode 20 to assure a uniform potential applied to the working electrode and to minimize ohmic-drop. The electrodes can have any shape, such as for example circular, rectangular or interdigitated. The electrodes are covered by a thin layer of ionic liquid 60. In the example shown in FIG. 1, the ionic liquid is trapped (at its lateral sides) by an epoxy structure 50 surrounding the electrode area. The ratio between the lateral size (e.g. width or diameter) of the working electrode and the height (thickness) of the ionic liquid thin layer is preferably as large as possible to achieve a large response of the sensor to an analyte, e.g. ethylene.

Although the electrochemical sensing element illustrated in FIG. 1 has a three-electrode configuration, the present disclosure is not limited thereto. For example, the electrochemical sensing element can have a two-electrode configuration (having a working electrode and a counter electrode) or it can have a four-electrode configuration (having two working electrodes, a counter electrode and a reference electrode).

In one embodiment, an electrochemical sensor further comprises electrical circuitry (not illustrated) for applying a voltage to the working electrode, for instance in the example shown in FIG. 1 the voltage may be applied by applying a voltage difference between the reference electrode and the working electrode. The electrical circuitry may also be configured for measuring a current between the working electrode and the counter electrode. The electrical circuitry is adapted for applying a voltage difference between the reference electrode and the working electrode in the range between about 700 mV before the onset of the oxidation of the working electrode material and the onset of oxidation of the working electrode material. In preferred embodiments the working electrode material is gold and the electrical circuitry is adapted for applying a voltage difference between the reference electrode and the working electrode in the range between about 700 mV before the onset of gold oxidation and the voltage difference corresponding to the onset of gold oxidation.

Figure 2:
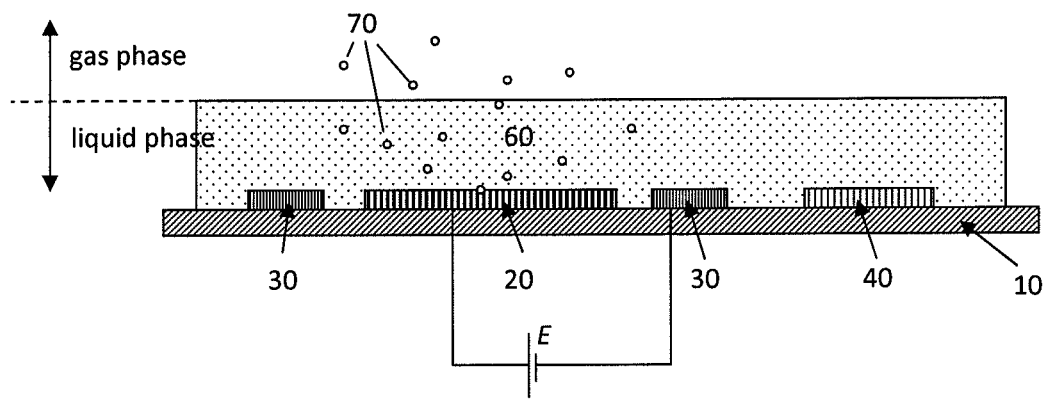
FIG. 2 is a schematic illustration of the ethylene sensing mechanism in accordance with one embodiment.

The sensing mechanism of a sensor according to one embodiment is schematically illustrated in FIG. 2. A gas to be detected, e.g. ethylene gas 70, dissolves in the thin ionic liquid layer 60 covering the gold working electrode 20 to which an oxidative potential E (voltage difference between the working electrode 20 and the reference electrode 30) is applied. The oxidative potential is selected such that it is in the range between about 700 mV before the onset of gold oxidation and the onset of gold oxidation. Preferably the oxidative potential is selected such that it is in the range between about 400 mV before the onset of gold oxidation and the onset of gold oxidation, e.g. at about 200 mV before the onset of gold oxidation. If such a potential E is applied the ethylene is oxidized at the working electrode 20, resulting in a current i between the working electrode 20 and the counter electrode 40.

Based on the current state-of-art, it is expected that this sensor is not capable of detecting ethylene. One would assume that the neutral pH of the ionic liquid prevents ethylene oxidation because of the formation of a gold oxide at the working electrode surface. However, the inventors surprisingly found that ethylene oxidation and thus ethylene detection and monitoring is possible with an ionic liquid based electrochemical sensor illustrated in FIG. 1.

Figure 4:
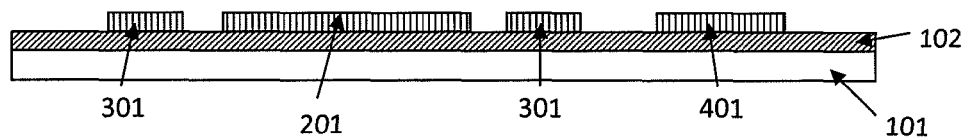
FIG. 4 shows cross-sectional views of the various stages in a fabrication process of a sensor according to one embodiment.
Figure 4:
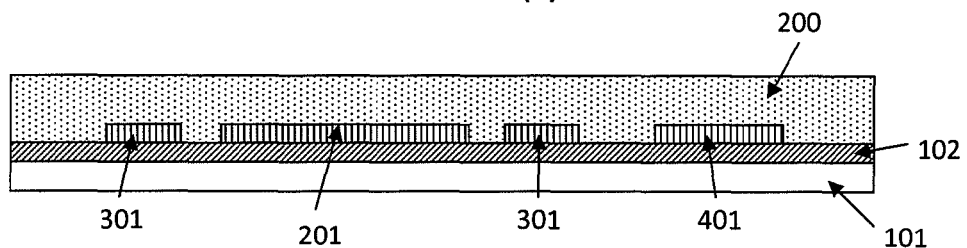
Figure 4:
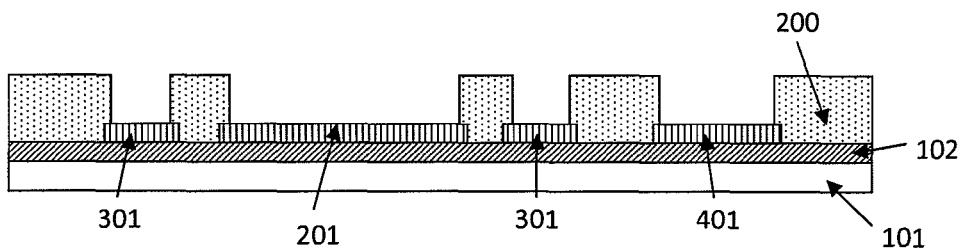
Figure 4:
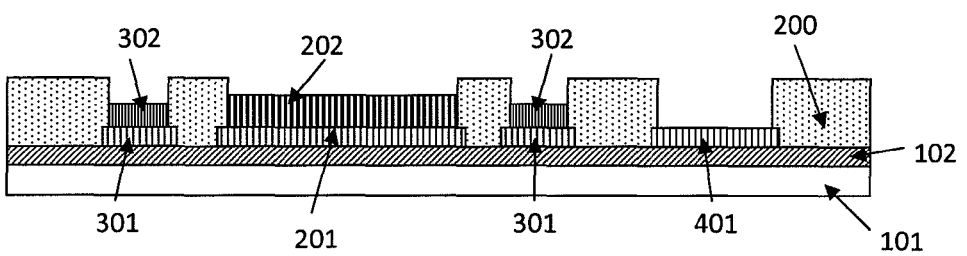
Figure 5:
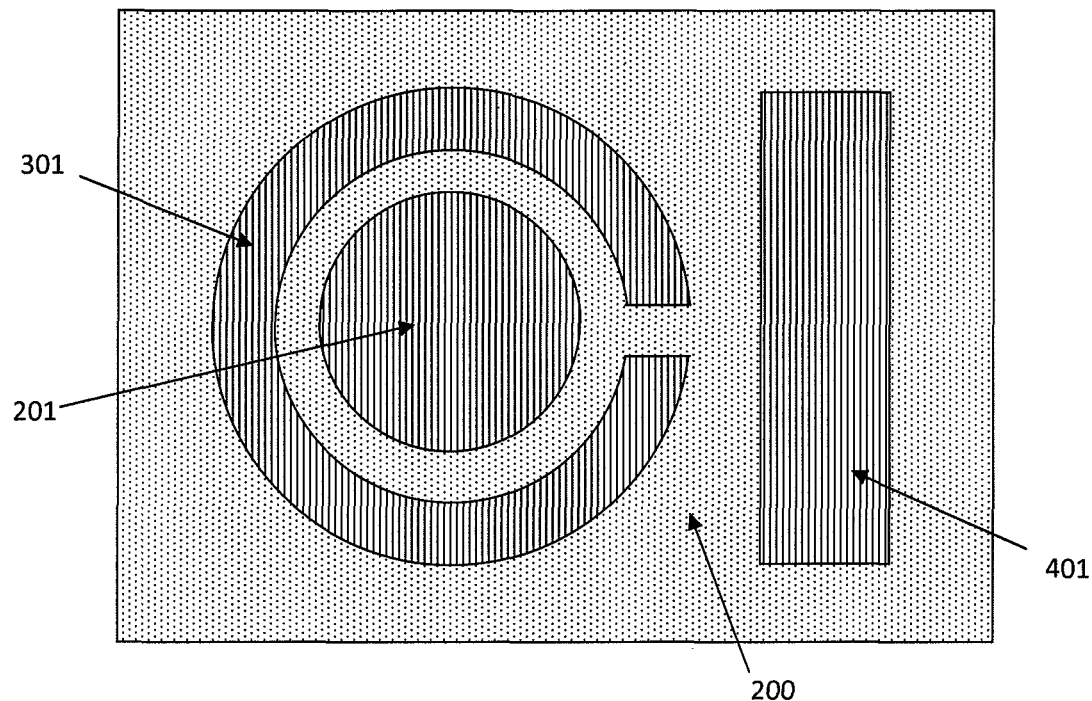
FIG. 5 shows top views of the various stages in a fabrication process of a sensor according to one embodiment.
Figure 5:
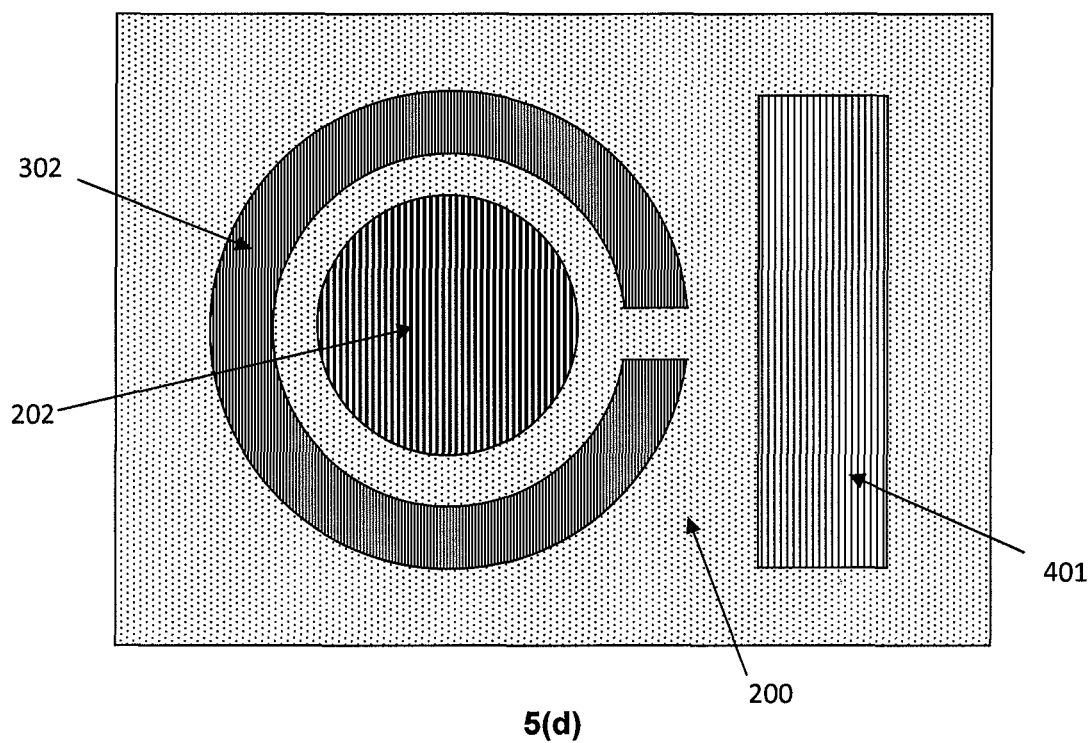

An ethylene sensor in accordance with one embodiment was fabricated according to the scheme illustrated in FIG. 4 (cross-sectional views) and FIG. 5 (top views). In a first step, illustrated in FIG. 4(a) and FIG. 5(a), a metal stack comprising an about 10 nm thick Ti adhesion layer and an about 100 nm thick Pt layer was provided by sputtering on a silicon wafer 101 covered with a 1 micrometer thick thermally grown $SiO_2$ insulating layer 102. The Ti and Pt layers were then patterned by photolithography and ion beam etching into a disk-shaped Pt working electrode (WE) pattern 201 with a radius of about 550 micrometer surrounded by a ring-shaped Pt reference electrode (REF) pattern 301 having an inner diameter of about 1200 micrometer and an outer diameter of about 2000 micrometer, an about 1800 micrometer long and about 500 micrometer wide rectangular counter electrode (CE) pattern 401, and feed wires (not illustrated) and bond pads (not illustrated). Next, as illustrated in FIG. 4(b) and FIG. 5(b), a NON layer 200 comprising a stack of about 200 nm SiN, about 600 nm $SiO_2$ and about 200 nm SiN was deposited by plasma enhanced chemical vapor deposition. The NON layer acts as a capping layer for the feed wires. Next, FIG. 4(c) and FIG. 5(c), openings were etched through the capping layer 200 in alignment with the working electrode pattern 201, the reference electrode pattern 301 and the counter electrode pattern 401 respectively. A disk-shaped opening with a radius of 500 micrometer was formed in the NON layer, the disk-shaped opening having its center point aligned with a center point of the underlying working electrode. Further, a ring-shaped opening with an inner diameter of about 1300 micrometer and an outer diameter of about 1900 micrometer was formed in the NON layer, the ring-shaped opening being aligned with the underlying reference electrode. Finally a rectangular opening with length about 1700 micrometer and width about 400 micrometer was etched through the capping layer, the rectangular opening being aligned with the underlying counter electrode. This step defines the size of the electrodes in the final device. Finally, as illustrated in FIG. 4(d) and FIG. 5(d), a patterned layer 202 comprising about 10 nm Ti and about 200 nm Au was deposited in the disk-shaped opening aligned with the WE pattern 201. A layer 302 comprising about 20 nm Cr and about 1 micrometer Ag was sputtered in the rectangular opening aligned with the REF pattern 301, both by photolithography and by lift-off. The present disclosure is however not limited to this process flow and these materials. For example, the bonding pads, CE and feed wires can comprise other metals such as for example gold or silver, and other suitable materials can be used for forming the working electrode and the reference electrode. This fabrication process provides good flexibility in choice of materials for the three electrodes.

The devices were then mounted and wire bonded in a dual in-line package (DIL package) and the edges and bond pads were covered by a chemically inert and acid resistant UV-curable epoxy (Epotek OG116-31). The epoxy also confines the ionic liquid on the chip to the sensor area, thus avoiding the ionic liquid from creeping over the edges, which would lead to unstable sensors.

In the experiments, the ionic liquids 1-butyl-3-methylimidazolium bis(trifluoromethylsulfonyl)imide ([BMIM] [$NTf_2$], cat. no. 491092) and 1-hexyl-3-methylimidazolium tris(pentafluoroethyl)trifluorophosphate ([HMIM][FAP], cat. no. 491078) were used in the highest available purity (halides about 100 ppm). Both ionic liquids were selected because of their ethylene absorption properties, their ability to absorb water and because they form stable films even when exposed to various humidities.

Before providing the ionic liquid, the working electrode was extensively cleaned by providing a droplet of a freshly prepared piranha solution (about 3:1 concentrated sulfuric acid:hydrogen peroxide) on the device for 5 minutes and rinsing with deionized water afterwards. The piranha solution however also etches Ag, thus removing the Ag layer from the reference electrode, leading to exposure of the underlying Pt. In the experiments, the reference electrode was therefore a Pt quasi-reference electrode. The harsh piranha cleaning was used in these experiments to remove any fabrication residues and to obtain reproducible results between devices. However, other suitable cleaning solutions that do not remove the Ag layer may be used.

Next, cyclic voltammetry between about −0.1 V vs. Pt and about 1.5 V vs. Pt (i.e. voltage difference between the working electrode and the Pt reference electrode between about −0.1 V and 1.5 V) in about 0.5 M sulfuric acid ($H_2SO_4$) with a scan rate of about 0.5 V/s or 0.1 V/s was performed until stable voltammograms were obtained that showed the characteristic behavior of gold. This technique was used to further clean the surface of the working electrode. In each cycle a monolayer of gold oxide is formed in the forward scan, after which the surface is turned back to gold in the backward scan. Doing so may desorb impurities from the surface. Furthermore, by stopping the sweeping in the right potential range (about 0.2 V to 0.5 V in the forward scan) the working electrode surface is free of gold oxide. The sensor was then rinsed with deionized water and with isopropanol and dried in a stream of nitrogen.

A thin ionic liquid layer was then provided covering the surface of the electrodes, using an Eppendorf about 0.1-2.5 microliter precision pipette. Sensors were fabricated with various ionic liquid amounts. The thickness of the ionic liquid layers was measured using a Leica Z16 APO microscope mounted on a Leica MDG28 motor drive. Polystyrene beads were dropped on the ionic liquid layer allowing focusing on the ionic liquid layer edge. The thickness of the ionic liquid layers was measured on at least about 10 different positions on the working electrode. Errors were partly related to the (about) 5 micrometer precision of the motor drive. Furthermore, the ionic liquid layer was slightly thicker close to the epoxy edges, probably due to meniscus formation. The average thickness was about 30 micrometer (about 7 micrometer standard deviation) when about 1 microliter of [HMIM][FAP] was provided onto the device; about 63 micrometer (about 17 micrometer standard deviation) when about 2 microliter of [HMIM][FAP] was provided onto the device; and about 142 micrometer (22 micrometer standard deviation) when about 4 microliter of [HMIM][FAP] was provided onto the device. These devices were further used for the recording of amperometric current versus time characteristics. For the devices used for cyclic voltammetry measurements, the average ionic liquid layer thickness was about 63 micrometer (about 10 micrometer standard deviation) for about 2 microliter of [BMIM][$NTf_2$] being provided onto the device. The average thickness was about three times thinner than expected from the area uncovered by the epoxy. This may be related to meniscus formation as mentioned before and to the uncertainty in the casted volume because the pipette was not calibrated for the viscous ionic liquids.

The devices were mounted in a custom build flow chamber and could be exposed to various ethylene concentrations in a nitrogen carrier flow. Part of the carrier flow was directed through water bubblers and mixed with dry nitrogen to control the humidity. The volume of the chamber was about 10 cm$^3$ and a mass flow controller was used to set the gas flow to about 150 sccm through the chamber.

Cyclic voltammograms (CVs) and amperometric current versus time responses were recorded with a CHI832c bipotentiostat (CH Instruments). The quiet time of the potentiostat was set to abut 10 s before recording the CVs and to about 45 s before recording the current-time responses.

Figure 6:
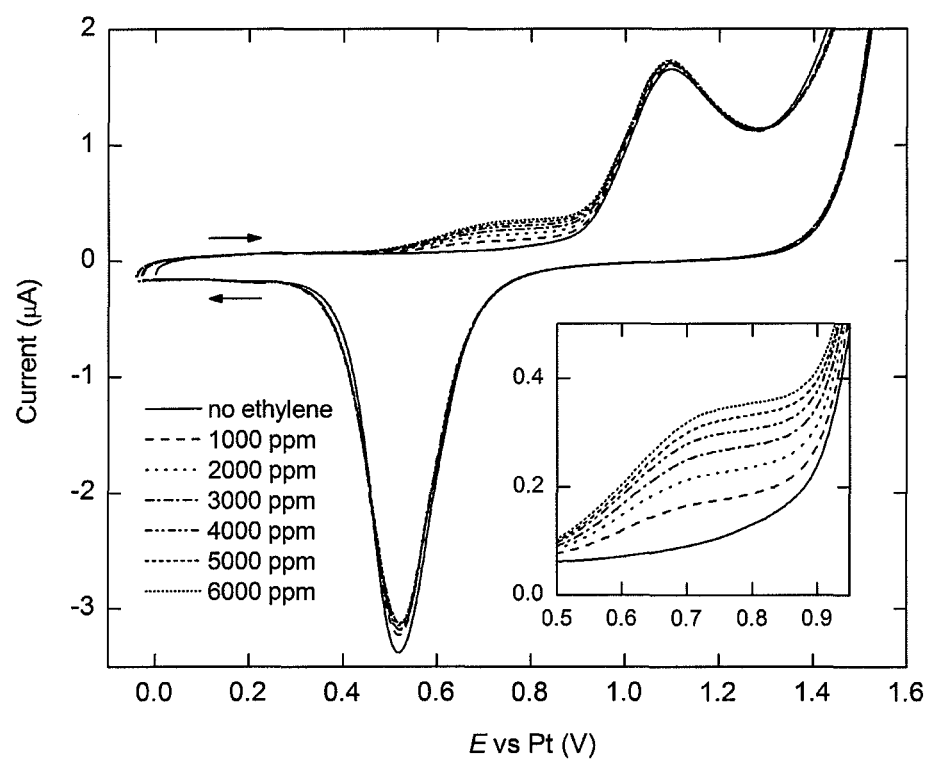
FIG. 6 shows current-voltage characteristics of a sensor according to one embodiment in the absence of ethylene (full line) and when exposed to various concentrations of ethylene (patterned lines) at 40% relative humidity.

FIG. 6 shows current-voltage characteristics (cyclic voltammograms, CVs with a scan rate of about 0.1 V/s) for a sensor according to one embodiment, the sensor comprising an about 63 micrometer thick layer of the ionic liquid [BMIM][NTf$_2$], in the absence of ethylene (full line) and when exposed to increasing concentrations of ethylene (patterned lines). The relative humidity was set to about 40% during the whole measurement. Thermogravimetric analysis (TGA) revealed that the uptake of water in this ionic liquid layer linearly scales with relative humidity. At about 40% relative humidity the ionic liquid layer contained about 274 mM of water. For the measurements in the absence of ethylene, no electrochemical reaction occurred in the forward scan until a voltage difference of about 0.9V between the working electrode and the reference electrode ('about 0.9V vs Pt'), after which the gold working electrode was oxidized. Above 1.3 V the current between the working electrode and the counter electrode rapidly increased due to water electrolysis. In the backward scan a large current dip (reduction peak) was observed between about 0.6 V and 0.4 V. This peak can be attributed to the reduction of the gold oxide layer formed in the forward scan. This peak was used as an internal reference because the quasi-reference electrode could drift during the experiment and the cyclic voltammograms of FIG. 6 were accordingly shifted with respect to the cyclic voltammogram measured in the absence of ethylene. The largest correction was about −42 mV for the cyclic voltammogram recorded for 6000 ppm ethylene. Cyclic voltammogram curves with identical features were obtained for the ionic liquid [HMIM][FAP] exposed to the same relative humidity (results not shown).

Figure 7:
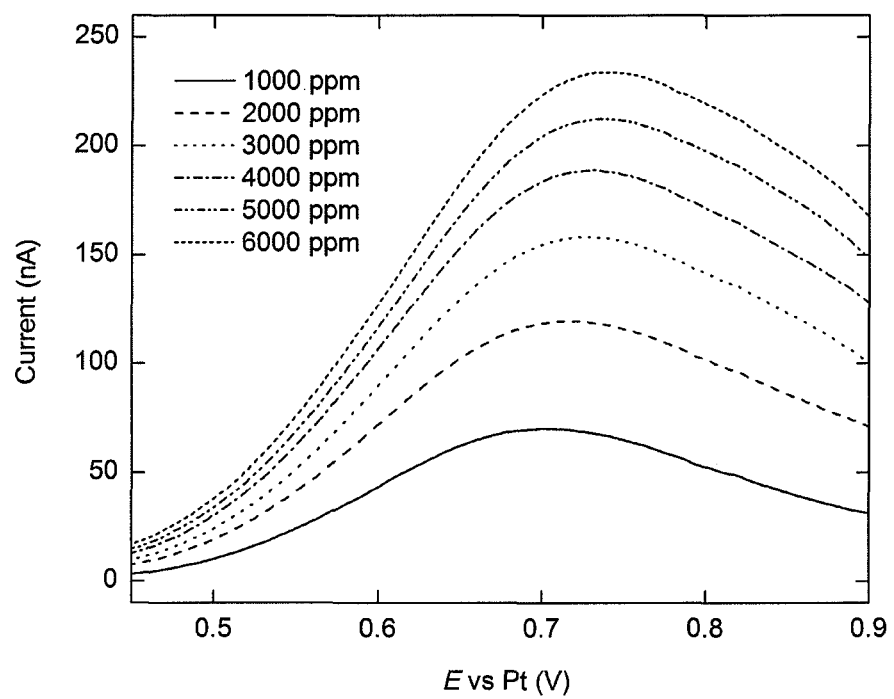
FIG. 7 shows the same potential region as the inset in FIG. 6 but corrected for the background current, revealing a peak in the ethylene oxidation.
Figure 8:
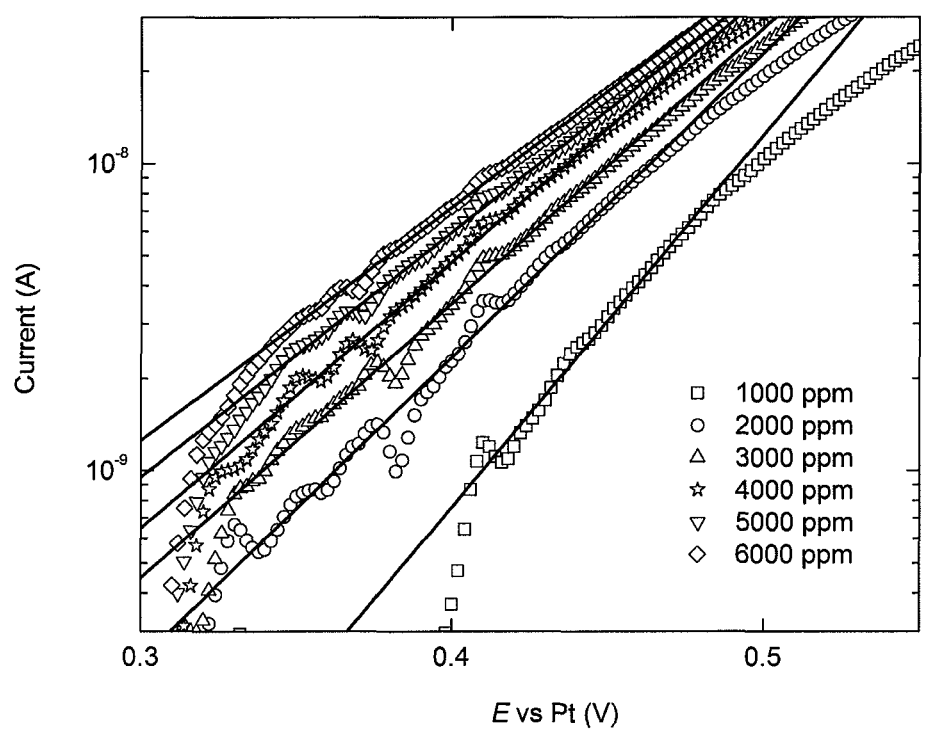
FIG. 8 shows Tafel plots of FIG. 7. The solid lines are linear fits.

When the sensor was exposed to ethylene, a current larger than the background (oxidation wave) was observed in the potential window between about 0.35 V and 0.9 V. The additional current gradually increases with concentration, as illustrated in FIG. 6. The inset in FIG. 6 is a magnification of the curves for the 0.5 V to 0.95 V range (forward scan). This additional current originates from ethylene that is oxidized at the working electrode surface. No reduction wave is observed, indicating that ethylene oxidation is chemically irreversible. In FIG. 7 the same curves are shown as in FIG. 6, but with the background current (i.e. the current in the absence of ethylene) subtracted. The resulting peak-like shape for the ethylene oxidation can be explained as follows. From the moment ethylene oxidation is possible (from about 0.35 V in the example shown) the current exponentially increased as can be seen in the Tafel plots of FIG. 8. The mean and standard deviations of 52 CVs recorded in three different humidities (20%, 40% and 60%) and for three identical devices were 132±42 mV. Above 0.5 V, the current started to deviate from the linear Tafel regime because of mass-transport limitation. The current further increased until gold oxide was formed on the surface (from about 0.7 V). The monolayer of gold oxide hindered the ethylene oxidation and the current decreased again. When the relative humidity was decreased to 0%, the gold oxidation and reduction peak diminished below the noise level of the sensor.

Figure 10:
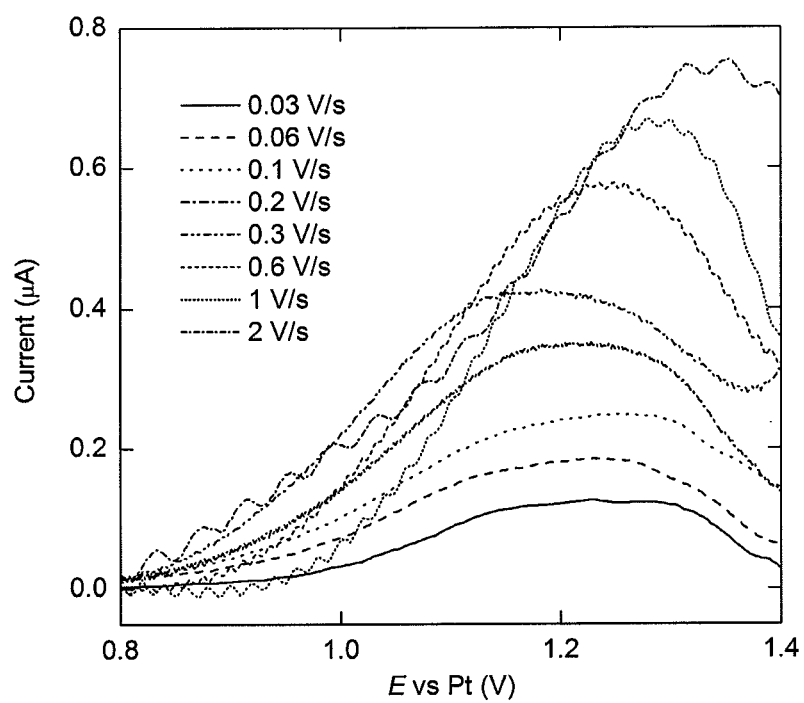
FIG. 10 shows cyclic voltammograms recorded in the presence of 3000 ppm ethylene for different scan rates, corrected for the background charging current.
Figure 11:
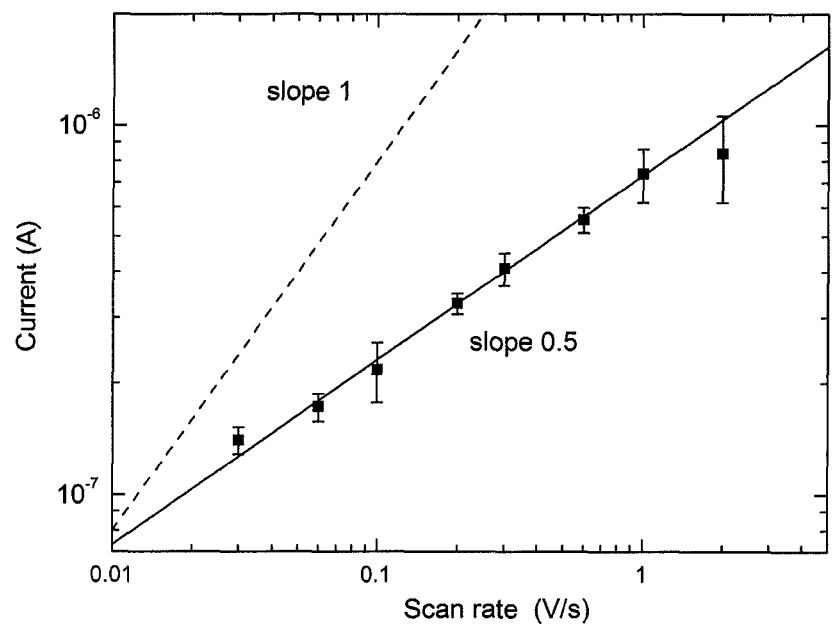
FIG. 11 shows the peak current corresponding to the curves shown in FIG. 10, as a function of scan rate.

This interpretation was further supported by cyclic voltammetry with varying scan rates v. In principle, a peak-shaped response (as in FIG. 7) could also be obtained for the oxidation of a strongly adsorbed layer or a finite amount of ethylene in the ionic liquid layer without replenishment from the gas phase. In both these cases, a linear dependence of the peak current as a function of scan rate is expected. FIG. 10 shows corrected cyclic voltammograms (after subtraction of the background current) recorded with different scan rates in the presence of about 3000 ppm ethylene. An ionic liquid layer of [BMIM][NTf$_2$] having a thickness of 63 micrometer was used. FIG. 11 shows the peak current as a function of scan rate. The symbols and error bars represent the mean and standard deviation of three different CVs recorded with the same device. It can be concluded that the peak current scales as $v^{1/2}$ up to 1 V/s (the solid line in FIG. 11 is a fit). At higher scan rates, the cyclic voltammograms were distorted due to significant ohmic drop and the peak current deviated from the square root dependence. The $v^{1/2}$-dependence confirmed that the peak shape originated from mass-transport limitation, followed by inhibition of the reaction by a monolayer of gold oxide.

Figure 9:
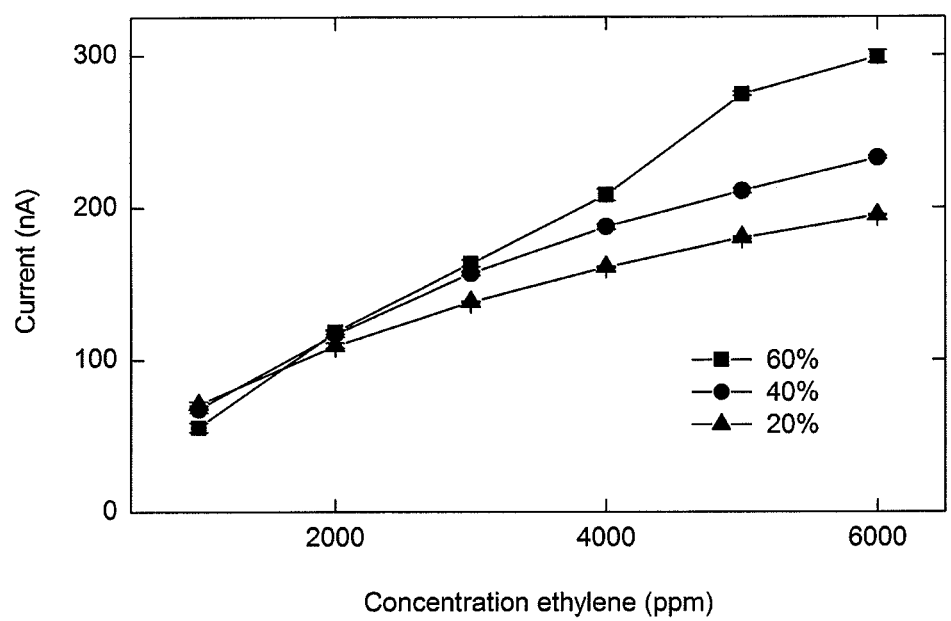
FIG. 9 shows the peak current as a function of ethylene concentration for different relative humidities (20%, 40% and 60%).

FIG. 9 shows the maximum current corresponding to FIG. 7 as a function of ethylene concentration for different relative humidities (20%, 40% and 60%). In between the measurements at different humidities the device was removed from the chamber and cleaned, thereby removing the ionic layer, and a new ionic liquid layer was provided to ensure identical starting conditions. For ethylene concentrations larger than 2000 ppm the response is largest at 60% relative humidity, followed by 40% and 20% relative humidity. This dependence may be caused by an altered diffusion coefficient, as described below. This behavior was observed for three different devices for which the order of recording the CVs was swapped.

Cyclic voltammetry is an appropriate technique for studying the reaction mechanism and kinetics. It is less suitable for sensor applications however because the cyclic voltammetry curves always need to be corrected for the background capacitive charging current and quantitative determination of the ethylene level is only obtained after data analysis. Furthermore, during each scan the gold surface is oxidized and reduced back. This might alter the catalytic properties and the area available for the reaction, which could lead to a different response for each consecutive cyclic voltammetry measurement.

Real-time sensitive determination of the ethylene concentration can be obtained by amperometry in which the potential difference between the working electrode and the reference electrode is fixed in a window in which ethylene is oxidized (and wherein the potential difference is below the onset of gold oxidation) and the current between the working electrode and the counter electrode is recorded as a function of time.

Figure 12:
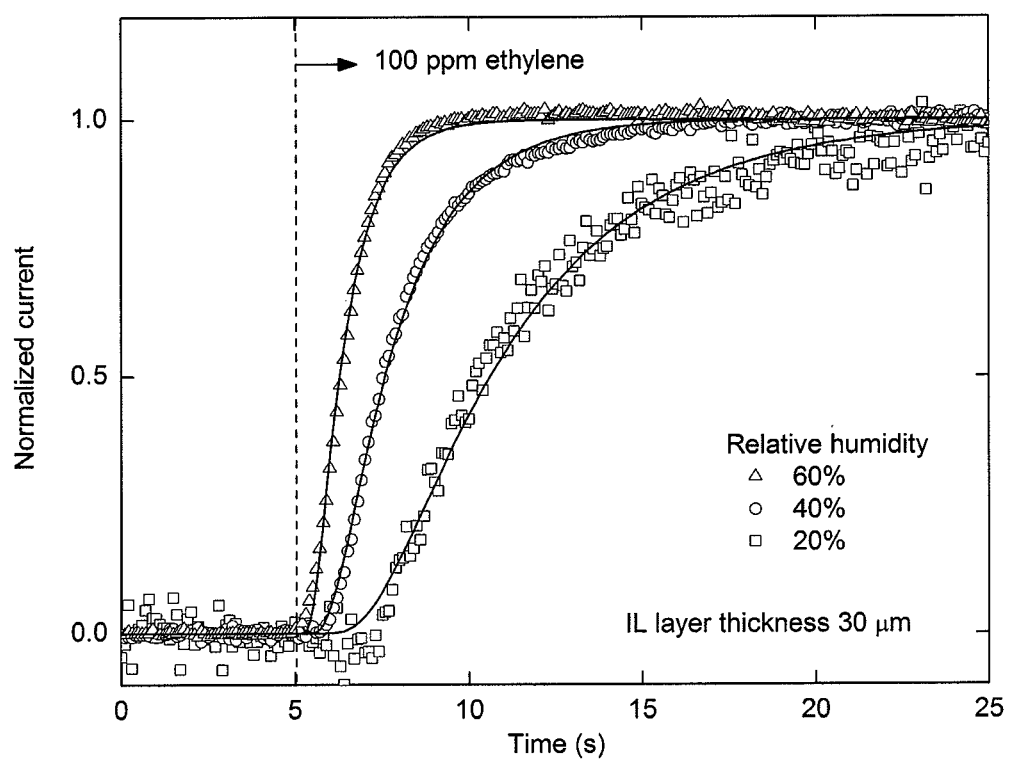
FIG. 12 shows normalized amperometric current-time responses after exposure to 100 ppm ethylene for three different relative humidities.
Figure 13:
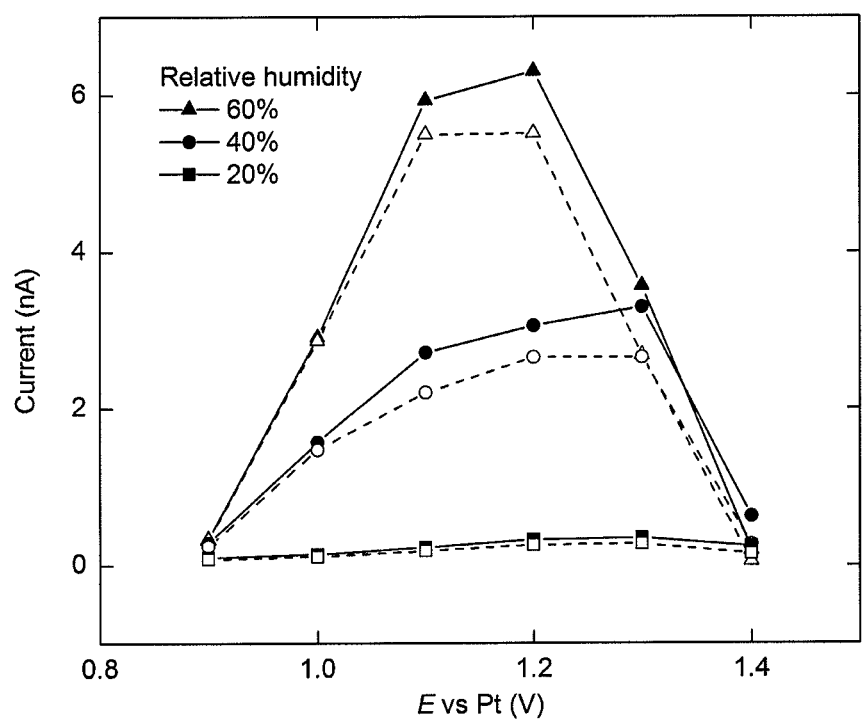
FIG. 13 shows steady-state currents as a function of applied potential for two consecutive steps. The closed symbols represent the first step; the open symbols represent the second step.

FIG. 12 shows amperometric current-time curves for a sensor according to one embodiment exposed to a step-wise increase of the ethylene concentration form 0 ppm to 100 ppm for three different relative humidities (20%, 40%, 60%). The applied potential was 1.2 V vs Pt for all humidities. The ionic liquid layer used was [HMIM][FAP] with a thickness of 30 micrometer. The responses are normalized by the plateau current ($i/i_s$) for better comparison. A small capacitive charging current still remained after the 45 s conditioning of the potentiostat. Therefore, each response was corrected by subtraction of an exponential fit of the background current in the absence of the 100 ppm ethylene. FIG. 13 shows the steady-state plateau current $i_s$ as a function of the applied potential during the recording of the response for the tree relative humidities investigated. The largest response is achieved in 60% relative humidity, followed by 40% and 20% relative humidity. The plateau current for two consecutive steps are shown: the closed symbols represent the first step, while the open symbols represent the second step. The current of the second step was in all cases smaller than the current of the first step. This may be related to slow gold oxide formation during the recording, thereby diminishing the active area available for the ethylene oxidation. A very similar plateau current-voltage dependence as shown in the corrected cyclic voltammograms of FIG. 7 was found: the current sharply increases from about 0.9 V and levels off around 1.1 V vs Pt due to mass-transport limitation. From 1.3 V the current significantly decreases because during the quiet time of the potentiostat (about 45 s) an appreciable amount of gold oxide is already formed.

The plateau current decreased when the relative humidity was decreased, while the time to reach 90% of the steady state current, $t_{90}$, increased from 2.6 s for 60% relative humidity to 5.0 s and 12.5 s for 40% relative humidity and 20% relative humidity respectively. This dependence can be interpreted as follows. Thermogravimetric analysis showed that the concentration of water in the ionic liquid [HMIM][FAP] scaled linearly with relative humidity. The water concentration was 27 mM, 53 mM and 80 mM for 20%, 40% and 60% relative humidity respectively. The presence of water decreases the viscosity of various ionic liquids and the Stokes-Einstein relation then predicts an increase of the diffusion coefficient D (although deviations for small molecules have been reported). Assuming that the device operates in the mass-transport limited regime, a linear dependence of the plateau current on the diffusion coefficient is expected and thus the plateau current is expected to be proportional to the relative humidity. Furthermore, the response time is expected to scale as $D^{-1}$. Both trends have been observed in the current-time responses displayed in FIG. 12.

Figure 14:
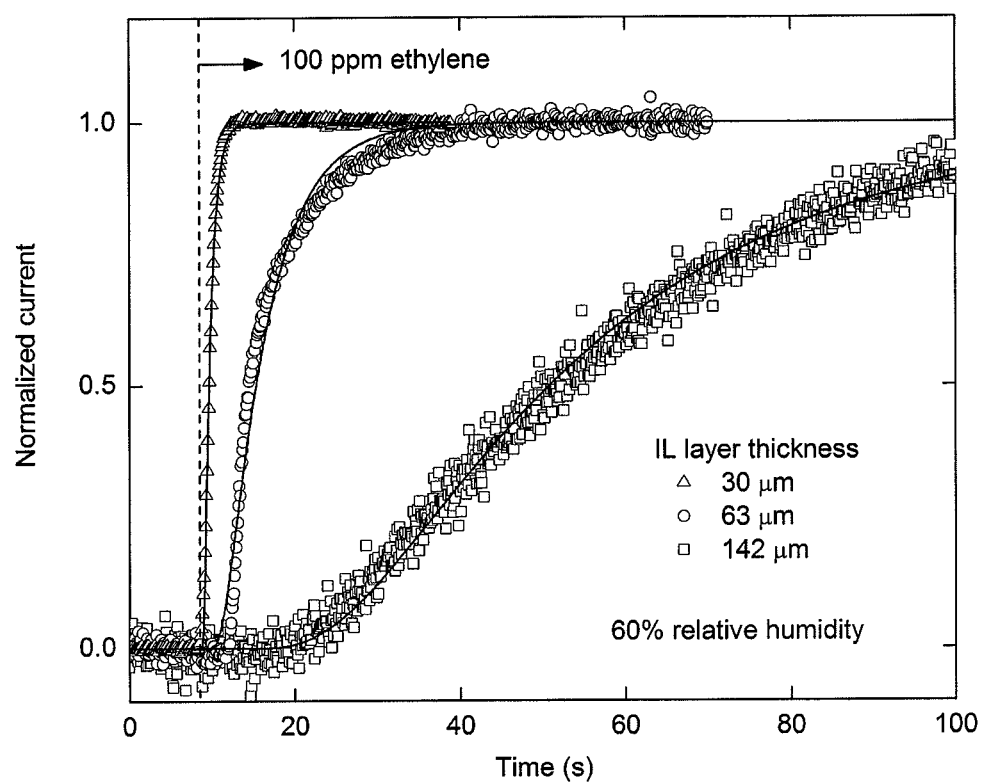
FIG. 14 shows the normalized step response to 100 ppm ethylene for three different ionic liquid layer thicknesses at 60% relative humidity.
Figure 15:
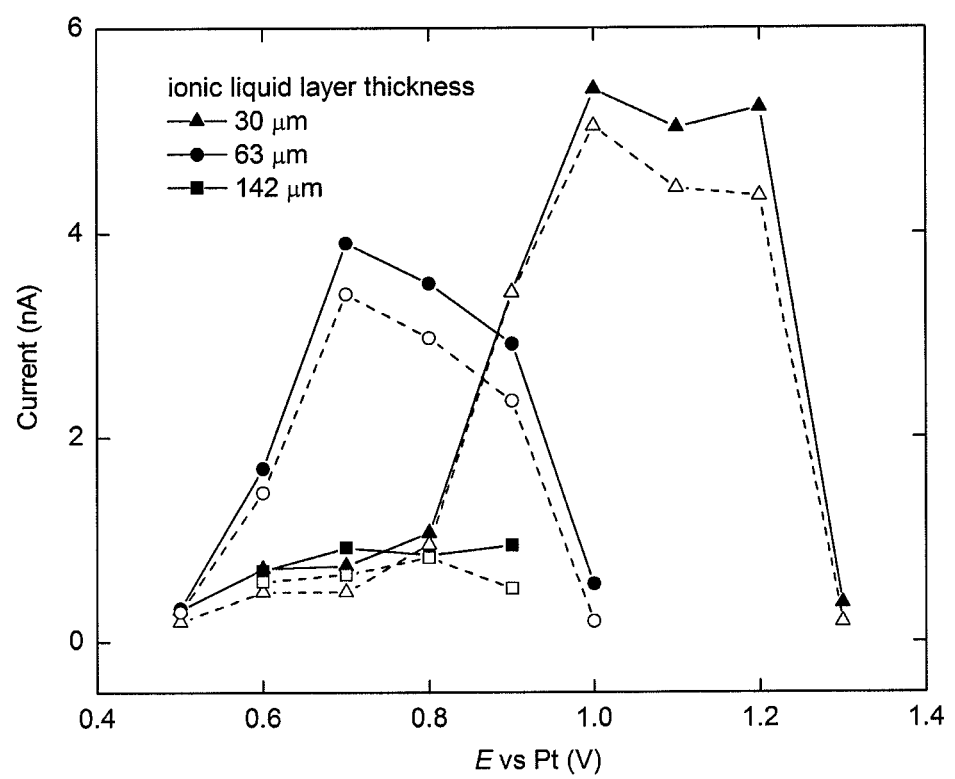
FIG. 15 shows steady-state currents as a function of the applied potential.

The assumption that the device operates in the mass-transport limited regime is further supported by a strong dependence of $i_s$ on the ionic layer thickness. FIG. 14 shows normalized step responses for devices with different thicknesses of the layer of [HMIM][FAP] ionic liquid. The ionic layer thickness was varied by casting 1 micro-liter, 2 micro-liter and 4 micro-liter respectively onto the device which resulted in a thickness of 30±7 micrometer, 63±17 micrometer and 142±22 micrometer, respectively. The relative humidity remained constant at 60%. The applied potential was 1.0 V vs Pt for the device with a 30 micrometer thick ionic liquid layer, 0.7 V vs Pt for a device with a 63 micrometer thick ionic liquid layer and 0.8 V vs Pt for a device with a 142 micrometer thick ionic liquid layer. The steady-state plateau current shown in FIG. 15 decreased by a factor of about 2 when the ionic liquid layer thickness was increased from 30 micrometer to 63 micrometer. When the ionic liquid layer thickness was increased 2.3 times to 142 micrometer, the current decreased by a factor of about 4 which cannot be explained by the theoretical model (the thin-layer model predicts that the current scales at most as L' wherein L is the thickness of the ionic liquid layer; a steeper decrease is not expected, even in the kinetically limited regime). The response time increased from 2.4 s to 17.5 s and 90 s for 30 micrometer, 63 micrometer and 142 micrometer thick ionic liquid layers respectively, which is faster than the $\sim L^2$ dependency expected. This discrepancy may be related to the ionic liquid layer not being uniform over the working electrode due to meniscus formation at the edges of the epoxy, such that the response diverges form the idealized thin-layer model. Furthermore, radial diffusion and convection can affect the response, especially for the largest ionic liquid layer thicknesses.

Figure 16:
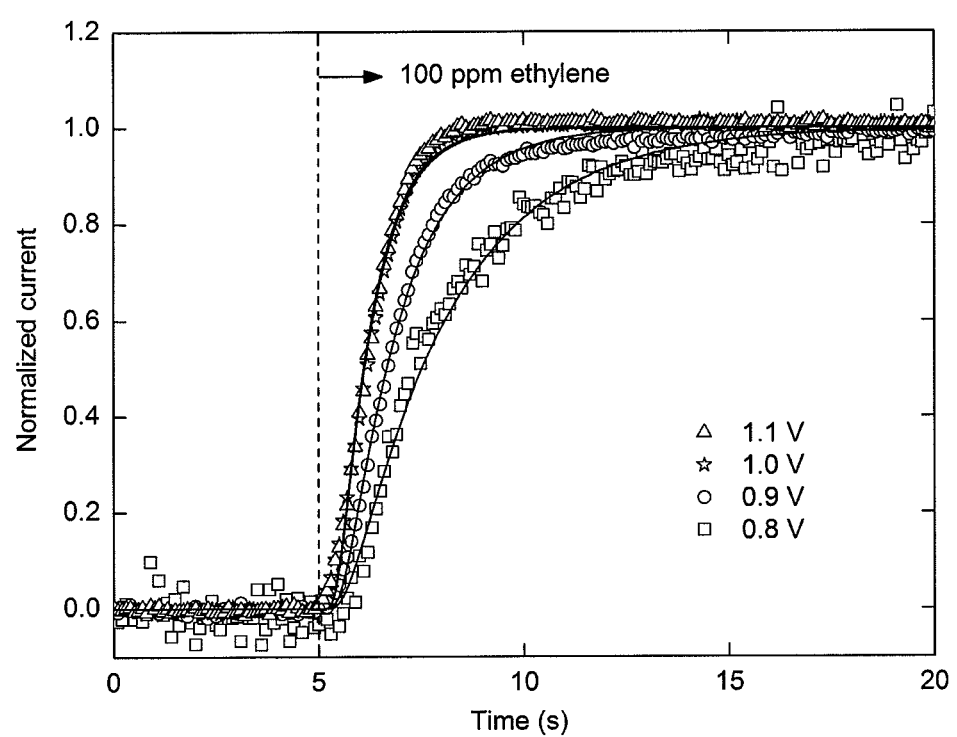
FIG. 16 shows normalized current-time responses as a function of applied potential for the same device as in FIG. 14 with an ionic layer thickness of 30 micrometer, at 60% relative humidity.

FIG. 16 shows normalized current-time responses for the same device as in FIG. 14 for different applied potentials. The ionic liquid layer thickness was 30 micrometer and the relative humidity was 60%. These voltages represent the region of FIG. 15 in which the current rises sharply until it levels off above 1.0 V. This coincides with the $t_{90}$ response time of FIG. 16 which decreased 3.3 times from 7.6 s for the response with applied potential 0.8 V to 2.3 s for the responses with applied potential 1.0 V and 1.1 V (these two responses are nearly indistinguishable). As soon as ethylene oxidation becomes possible, the current is kinetically limited and increases exponentially with applied potential. When the mass-transfer rate becomes comparable to the electron-transfer rate, the current levels off and a steady-state plateau is reached when the current is fully mass-transport limited. The response time for the normalized current decreases from $\tau=4L^2/\pi^2 D$ in the kinetically limited regime to $\tau=L^2/\pi^2 D$ in the mass-transport limited regime. Since L and D remained constant (the relative humidity was kept constant) a factor of 4 difference was expected. The different response times thus originated from the different regimes in which the device operated. The response recorded at 0.9 V represented an intermediate regime, in which the mass-transport was comparable to the electron-transfer kinetics. The sensor response time decreased with increasing applied voltage, which is caused by a crossover from the kinetically limited regime to the mass-transport limited regime.

Figure 17:
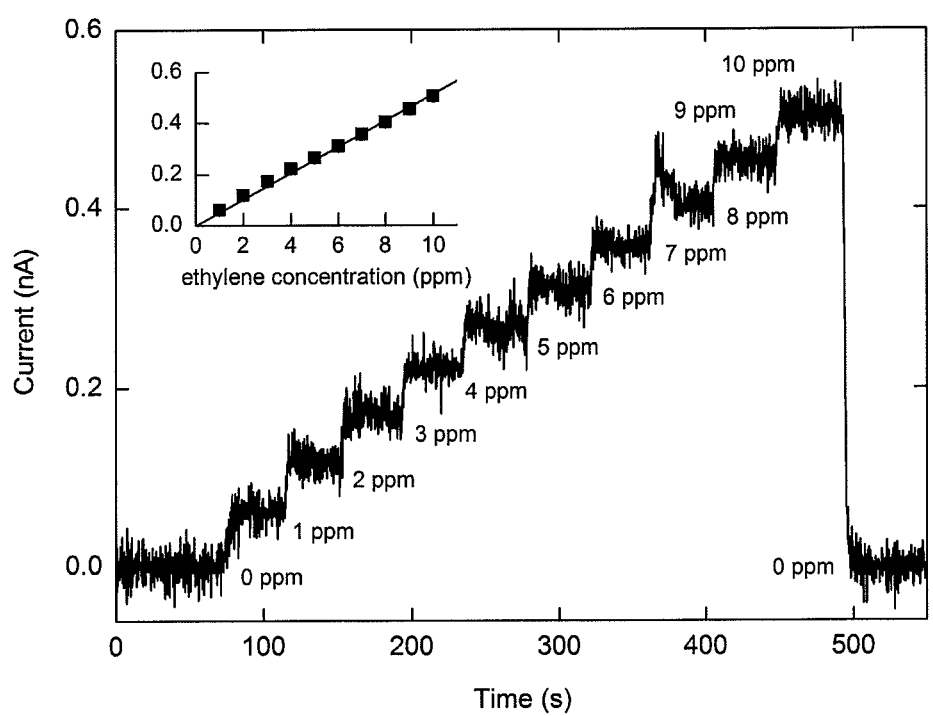
FIG. 17 shows current versus time during exposure of a sensor according to one embodiment to step-wise increasing concentrations of ethylene.

The largest absolute response was obtained for the thinnest ionic liquid layer (30 micrometer) and the highest relative humidity (60%) with the device operating in the mass-transport limited regime (applied potential about 200 mV before the onset of gold oxidation). Under these ideal circumstances, the limit of ethylene sensitivity was explored. FIG. 17 shows amperometric current-time responses for a sensor according to one embodiment, the sensor being exposed to 1 ppm stepwise increments of ethylene concentration. The steps could be clearly identified in the current and scaled linearly with concentration (in contrast to cyclic voltammetry with about 100 fold higher concentrations). This can be seen in the inset of FIG. 16 which shows the plateau current as a function of ethylene concentration. The solid line is a linear fit with slope 51 pA/ppm. The detection limit achieved was 760 ppb based on a signal to noise ratio of 3. Further device optimization, such as for example the use of thinner ionic liquid layers, the use of ionic liquid gels and/or adding e.g. silver salt to the ionic liquid, is expected to result in a lower detection limit.

Figure 18:
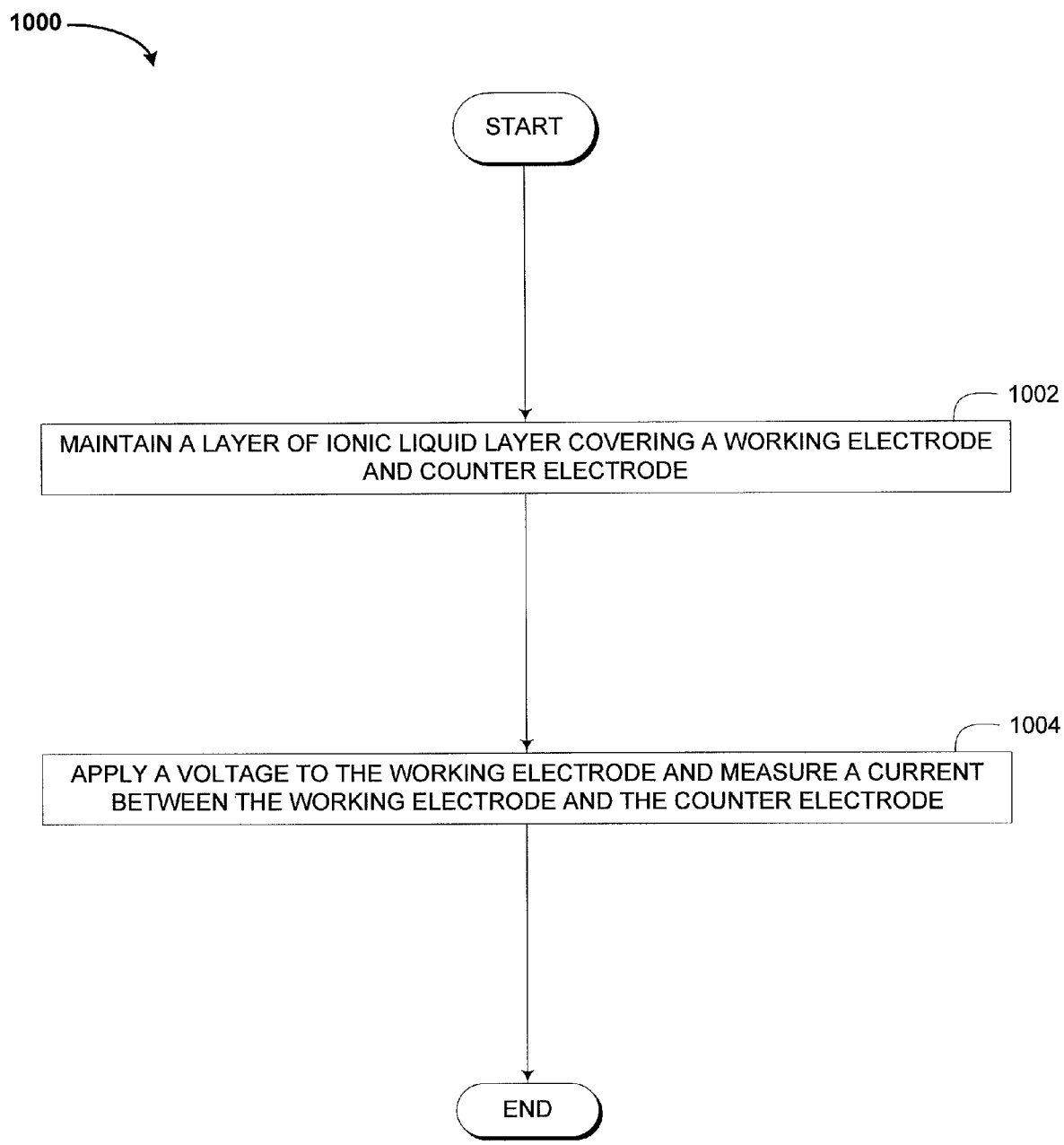
FIG. 18 shows a flowchart of one embodiment of a method of monitoring ethylene.

FIG. 18 shows a flowchart of one embodiment of a method of monitoring ethylene. The method 1000 includes, at block 1002, maintaining a layer of ionic liquid layer covering a working electrode and counter electrode. The method 1000 further includes, at block 1004, applying a voltage to the working electrode and measuring a current between the working electrode and the counter electrode.

Although systems and methods as disclosed, is embodied in the form of various discrete functional blocks, the system may be embodied in an arrangement in which the functions of any one or more of those blocks or indeed, all of the functions thereof, are realized, for example, by one or more appropriately programmed processors or devices.

It is to be noted that the processor or processors may be a general purpose, or a special purpose processor, and may be for inclusion in a device, e.g., a chip that has other components that perform other functions. Thus, one or more aspects of the present invention can be implemented in digital electronic circuitry, or in computer hardware, firmware, software, or in combinations of them. Furthermore, aspects of the invention can be implemented in a computer program product stored in a computer-readable medium for execution by a programmable processor. Method steps of aspects of the invention may be performed by a programmable processor executing instructions to perform functions of those aspects of the invention, e.g., by operating on input data and generating output data. Accordingly, the embodiment includes a computer program product which provides the functionality of any of the methods described above when executed on a computing device. Further, the embodiment includes a data carrier such as for example a CD-ROM or a diskette which stores the computer product in a machine-readable form and which executes at least one of the methods described above when executed on a computing device.

The foregoing description details certain embodiments of the invention. It will be appreciated, however, that no matter how detailed the foregoing appears in text, the invention may be practiced in many ways. It should be noted that the use of particular terminology when describing certain features or aspects of the invention should not be taken to imply that the terminology is being re-defined herein to be restricted to including any specific characteristics of the features or aspects of the invention with which that terminology is associated.

While the above detailed description has shown, described, and pointed out novel features of the invention as applied to various embodiments, it will be understood that various omissions, substitutions, and changes in the form and details of the device or process illustrated may be made by those skilled in the technology without departing from the spirit of the invention.

What is claimed is:

1. An electrochemical ethylene sensor comprising:
a plurality of electrodes formed on an electrically insulating substrate, the plurality of electrodes comprising a working electrode, a reference electrode and a counter electrode; and
an ionic liquid layer covering the plurality of electrodes,
wherein the working electrode and the counter electrode are configured for measuring a current flowing therebetween in response to a positive voltage applied between the working electrode and the reference electrode, wherein the positive voltage has a magnitude below a first voltage at which an onset of oxidation of the working electrode occurs by at least 200 mV,
wherein the ionic liquid layer has a neutral pH, has a solubility of ethylene exceeding about 0.1 mol % and has ethylene dissolved therein, is adapted to absorb water up to 5 wt. % and has water absorbed therein, and has a viscosity between 1 mPa s and 500 mPa s,
such that a second voltage at which an onset of oxidation of the dissolved ethylene occurs is lower than the first voltage, and that the sensor generates a current resulting from oxidation of ethylene in response to the positive voltage.

2. The electrochemical ethylene sensor as claimed in claim 1, further comprising electrical circuitry configured to apply the voltage between the working electrode and the reference electrode, wherein the applied voltage is equal to or below the voltage that leads to onset of oxidation of the working electrode.

3. The electrochemical ethylene sensor as claimed in claim 2, wherein the electrical circuitry is configured to apply a voltage in the range between about 700 mV before the onset of oxidation of the working electrode and the onset of oxidation of the working electrode.

4. The electrochemical ethylene sensor as claimed in claim 2, wherein the electrical circuitry is configured to measure the current between the working electrode and the counter electrode.

5. The electrochemical ethylene sensor as claimed in claim 1, wherein the working electrode comprises one of gold, iridium, palladium, rhodium, osmium, ruthenium platinum or glassy carbon.

6. The electrochemical ethylene sensor as claimed in claim 5, wherein the working electrode comprises gold.

7. The electrochemical ethylene sensor as claimed in claim 1, wherein the sensor has a size in the range between about 10 mm$^2$ and 25 mm$^2$.

8. The electrochemical ethylene sensor as claimed in claim 1, wherein the thickness of the ionic liquid layer is in the range between about 1 nm and about 100 micrometer.

9. The electrochemical ethylene sensor as claimed in claim 1, wherein the sensor has an ethylene detection limit of lower than about 1000 ppb.

10. The electrochemical ethylene sensor as claimed in claim 1, wherein the ionic liquid layer comprises an ionic liquid gel.

11. The electrochemical ethylene sensor as claimed in claim 1, wherein the ionic liquid layer comprises silver salt additive.

12. The ethylene sensor of claim 1, wherein the ionic liquid layer is configured to absorb up to about 5 percent by weight of water without affecting the stability of the ionic liquid layer.

13. The ethylene sensor of claim 12, wherein the ionic liquid layer is stable when exposed to air.

14. The electrochemical ethylene sensor as claimed in claim 1, wherein the ionic liquid comprises a liquid selected from the group consisting of 1-butyl-3-methylimidazolium bis(trifluoromethylsulfonyl)imide ([BMIM][NTf$_2$]) and 1-hexyl-3-methylimidazolium tris(pentafluoroethyl)trifluorophosphate ([HMIM][FAP]).

15. The electrochemical ethylene sensor as claimed in claim 14, wherein the ionic liquid further comprises a crosslinked polymer.

16. A system for monitoring ethylene, the system comprising:
means for maintaining a layer of ionic liquid layer covering a working electrode and counter electrode; and
means for applying a positive voltage to the working electrode and measuring a current between the working electrode and the counter electrode, wherein the positive voltage has a magnitude below a first voltage at which an onset of oxidation of the working electrode occurs,
wherein the ionic liquid layer has a neutral pH, has a solubility of ethylene exceeding about 0.1 mol % and has ethylene dissolved therein, is adapted to absorb water up to 5 wt. % and has water absorbed therein, and has a viscosity between 1 mPa s and 500 mPa s,
such that a second voltage at which an onset of oxidation of the dissolved ethylene occurs is lower than the first voltage, and that the system generates a current resulting from oxidation of ethylene in response to the positive voltage.

17. An electrochemical ethylene sensor, comprising:
an insulating substrate;
a liquid confinement area configured to hold an ionic liquid over the insulating substrate;

first, second and third electrodes formed on the insulating substrate and configured to be in contact with the ionic liquid, wherein the first and third electrodes are configured for measuring a current flowing therebetween in response to a positive voltage applied between the first and second electrodes, wherein the positive voltage has a magnitude below a first voltage at which an onset of oxidation of the working electrode occurs, wherein when the liquid confinement area holds the ionic liquid, wherein the ionic liquid has a neutral pH, has a solubility of ethylene exceeding about 0.1 mol % and has ethylene dissolved therein, is adapted to absorb water up to 5 wt. % and has water absorbed therein, and has a viscosity between 1 mPa s and 500 mPa s, such that a second voltage at which an onset of oxidation of the dissolved ethylene occurs is lower than the first voltage, and that the sensor generates a current resulting from oxidation of ethylene in response to the positive voltage.

18. The sensor of claim 17, further comprising a sensing circuit configured to sense the current flowing between first and third electrodes, wherein the current comprises current from oxidation of the analyte dissolved in the ionic liquid.

19. The sensor of claim 18, further comprising a voltage source configured to apply the voltage between first and second electrodes within a voltage range between an oxidation potential of the analyte and an oxidation potential of the first electrode, such that the sensor is configured to sense the current from oxidation of the analyte without oxidizing the first electrode.

* * * * *